(12) United States Patent
Wilk

(10) Patent No.: US 6,429,431 B1
(45) Date of Patent: Aug. 6, 2002

(54) MEDICAL DIAGNOSTIC METHOD AND APPARATUS UTILIZING RADIOACTIVITY DETECTION

(76) Inventor: Peter J. Wilk, 185 West End Ave., New York, NY (US) 10023

( * ) Notice: Subject to any disclaimer, the term of this patent is extended or adjusted under 35 U.S.C. 154(b) by 0 days.

(21) Appl. No.: 09/405,852

(22) Filed: Sep. 24, 1999

(51) Int. Cl.$^7$ .................................................. G01T 1/24
(52) U.S. Cl. ............................ 250/363.02; 250/363.01
(58) Field of Search ....................... 250/363.02, 363.01, 250/363.03, 363.04, 370.01, 370.09, 370.14, 366, 367, 369

(56) References Cited

U.S. PATENT DOCUMENTS

| | | | | |
|---|---|---|---|---|
| 4,672,207 A | * | 6/1987 | Derenzo | 250/363 |
| 5,117,114 A | * | 5/1992 | Street et al. | 250/370.11 |
| 5,821,541 A | * | 10/1998 | Tumer | 250/370.09 |
| 6,080,989 A | * | 6/2000 | Royle et al. | 250/366 |

\* cited by examiner

Primary Examiner—Constantine Hannaher
Assistant Examiner—Otilia Gabor
(74) Attorney, Agent, or Firm—R. Neil Sudol; Coleman, Sudol, Sapone, P.C.

(57) ABSTRACT

A medical diagnostic apparatus includes a carrier body, a plurality of rigid substrates each bearing at least one solid-state gamma ray sensor, the substrates being attached to the carrier body, and a computer operatively connected to the sensors for receiving signals therefrom and deriving information about location and size of a source of radioactivity in the patient. The carrier body enables disposition of different gamma ray sensors on different sides of the patient so that the sensors at least partially surround the patient. In an associated medical diagnostic method, a chemical composition containing a radioactive isotope is administered to a patient. A plurality of solid-state sensors sensitive to gamma rays generated by radioactive decay of the isotope are subsequently disposed about the patient, and signals from the sensors are conducted to a computer, which is then operated to derive information about location and size of a source of radioactivity in the patient. The sensors may be mounted to a flexible web which is manipulated to conform to the patient.

17 Claims, 6 Drawing Sheets

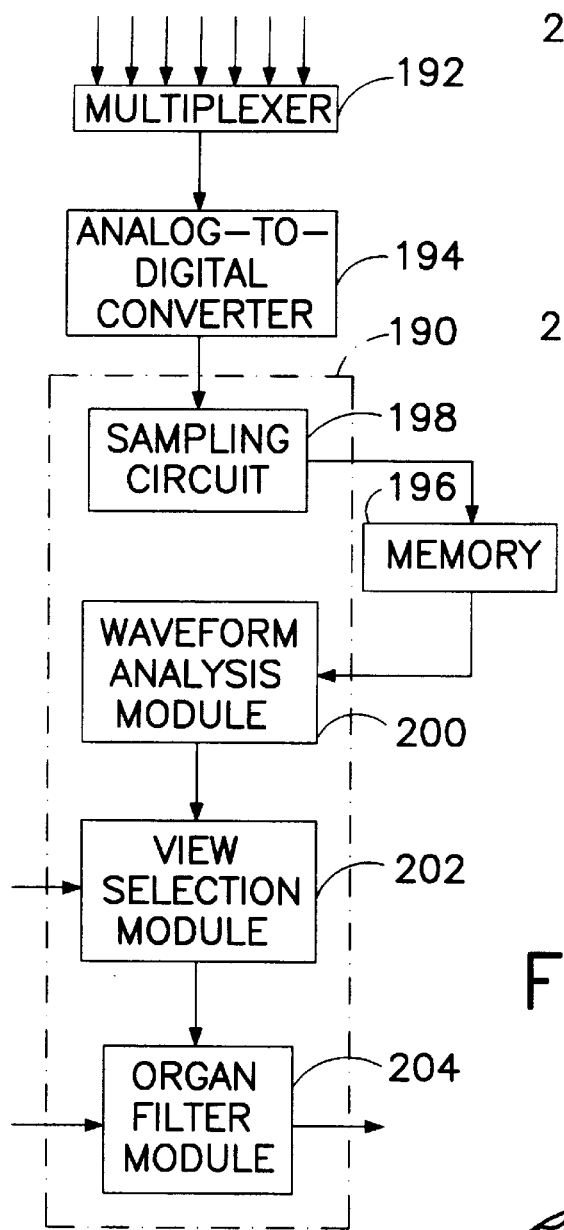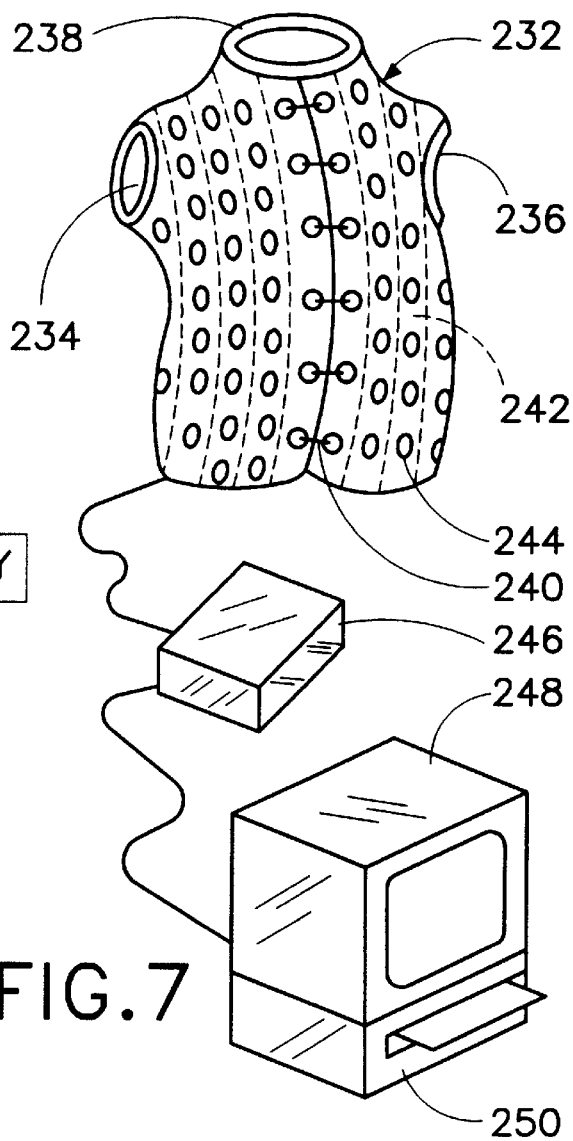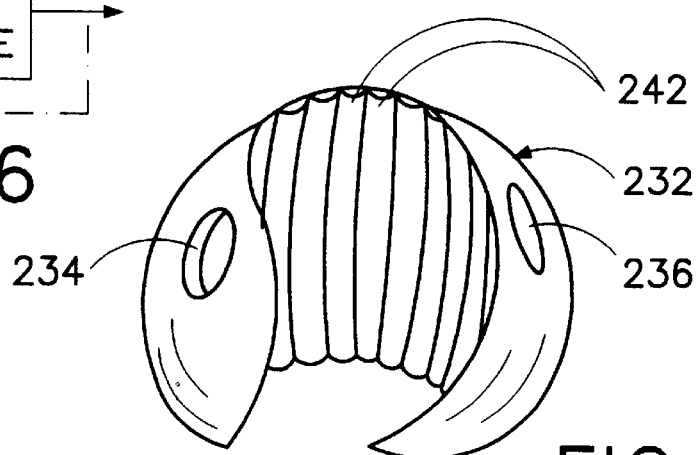

MEDICAL DIAGNOSTIC METHOD AND APPARATUS UTILIZING RADIOACTIVITY DETECTION

BACKGROUND OF THE INVENTION

This invention relates to the field of nuclear medicine. More particularly, this invention relates to an apparatus and to an associated method for detecting sources of radioactivity inside a patient for diagnostic purposes.

"Nuclear medicine" refers in part to that branch of the medical field which uses various types of radioactive isotopes to detect internal organic and histological defects in a patient. Generally, a chemical composition incorporating a radioactive isotope is injected or otherwise administered to a patient and, after a sufficient period to allow absorption of the composition by target tissues, the patient is scanned to detect whether and to what extent the chemical composition has been absorbed. For example, in determining whether a person has a tumor of the thyroid, radioactive potassium iodide is administered to the person and, after the lapse of a predetermined migration and absorption period, the person is positioned on a table below a detector tuned to sense radioactive emissions of the iodide isotope.

A problem with conventional nuclear medicine procedures is the high mortality rate. More specifically, because the patients subjected to such diagnostic procedures are very ill, and because the technicians operating the nuclear medicine equipment are not trained as doctors, many patients die during the testing procedures.

OBJECTS OF THE INVENTION

An object of the present invention is to provide an apparatus for detecting radioactive isotopes in a patient.

Another object of the present invention is to provide such an apparatus which is of reduced size relative to conventional nuclear medicine detectors.

A more particular object of the present invention is to provide such an apparatus which is portable.

It is another particular object of the present invention to provide such an apparatus which is capable of being used in an intensive care unit of a hospital facility.

It is an additional object of the present invention to provide an associated nuclear medicine diagnostic method.

These and other objects of the present invention will be apparent from the drawings and descriptions herein.

SUMMARY OF THE INVENTION

A medical diagnostic apparatus comprises, in accordance with the present invention, a carrier body, a plurality of rigid substrates each bearing at least one solid-state gamma ray sensor, the substrates being attached to the carrier body, and a computer operatively connected to the sensors for receiving signals therefrom and deriving information about location and size of a source of radioactivity in the patient. The carrier body enables disposition of different gamma ray sensors on different sides of the patient so that the sensors at least partially surround the patient.

In accordance with a main embodiment of the present invention, the carrier body is flexible and substantially conformable to a patient. The carrier body may specifically take the. form of a flexible web which may be wrapped around a patient in a generally cylindrical configuration having a diameter which depends on the size of the particular portion of a patient which is being investigated via radioactive tagging.

Generally, as in conventional nuclear medicine investigations, the patient is supplied with a radioactive composition which is keyed for take-up or absorption by a particular organ of the body. In this case, the mere detection of a source in the body indicates that the target zone or organ has absorbed the composition. The target zone, and hence the location of the radioactive source (target tissues), is known before hand. The extent of the absorption may be measured by the medical diagnostic apparatus of the present invention.

A medical diagnostic system in accordance with the present invention may also be used for determining the shape, size, and location of an organic tissue body which has absorbed or acquired a radioactively tagged composition. In that case, it is advantageous to know the positions of the various solid-state gamma ray sensors relative to one another upon juxtaposition of the carrier body to the patient. These positions will be known as a matter of course if the carrier body is rigid. A rigid carrier body may take a semicylindrical form, such as a slotted collar or sleeve. Alternatively, where the carrier body is flexible or otherwise internally shiftable, an active sensing system may be provided for enabling determination of the positions of the gamma ray sensors relative to one another and relative to the patient. Generally, this sensing system is operatively connected to the computer for providing position information thereto. The computer itself is programmed to determine relative positions of the gamma ray sensors from the incoming position information.

Where the shape and size of a source of radioactive emissions is determinable as disclosed herein, the location of a source of radioactivity in a patient may be determined by comparing the detected shape and size of the source with the shapes and sizes of expected target zones or organs.

In the case of a flexible or internally movable carrier body, the position sensing system may be optical. For example, interferometric metrology devices may be attached to substrates of the gamma ray sensors for measuring changes in positions of adjacent sensors. Alternatively, the carrier body may be illuminated with an optical grid which is distorted due to the irregular surfaces of the carrier body and the patient. An image captured by one or more cameras is analyzed by computer to determine the shape causing the distortions in the apparent shape of the optically generated grid.

A related medical diagnostic device comprises, in accordance with the present invention, a plurality of solid-state radioactivity sensors and a carrier attached to the sensors for enabling disposition of the sensors in a nonplanar configuration so as to at least partially surround a portion of a patient.

In accordance with another feature of the present invention, the carrier specifically takes the form of at least one movable connector element attached to the sensors for movably coupling the sensors to one another. The sensors may be movably attached to one another so as to allow at least a pivoting motion of each sensor relatively to a respective one other of the sensors. In a particular embodiment of the present invention, the connector element is a flexible substrate or web conformable to a skin surface of a patient, the sensors being attached in a predetermined array to the flexible substrate.

The sensors have output leads operatively connected to a computer programmed to derive information about location and size of a source of radioactivity in the patient.

An associated medical diagnostic method comprises, in accordance with the present invention, administering to a patient a chemical composition containing a radioactive isotope, thereafter disposing about the patient a plurality of solid-state sensors sensitive to gamma rays generated by radioactive decay of the isotope, conducting signals from the sensors to a computer, and operating the computer to derive information about location and size of a source of radioactivity in the patient.

Pursuant to a feature of the present invention, at least two of the sensors are positioned on different sides of the patient. Ideally, the sensors are distributed so as to surround the patient. The sensors may be placed in essential contact with the patient, for example, where the sensors are attached to a flexible web which is manipulated to conform to the patient.

The present invention provides an apparatus useful in medical diagnostic procedures and more particularly useful in medical diagnostic procedures wherein radioactive isotopes are administered to a patient.

The apparatus of the present invention is of reduced size relative to conventional nuclear medicine detectors. More specifically, an apparatus in accordance with the present invention may be designed for portability.

An apparatus and an associated method in accordance with the present invention are capable of being used in an intensive care unit of a hospital facility.

BRIEF DESCRIPTION OF THE DRAWINGS

FIG. 6 is a block diagram showing a modification of the ultrasonic imaging system illustrated in FIG. 5.

FIG. 7 is a schematic perspective view of another nuclear medicine diagnostic apparatus in accordance with the present invention, showing a sensor vest in a closed, use configuration.

FIG. 8 is a schematic perspective view of the sensor vest of FIG. 7, showing the vest in an open configuration.

DESCRIPTION OF THE PREFERRED EMBODIMENTS

Figure 1:
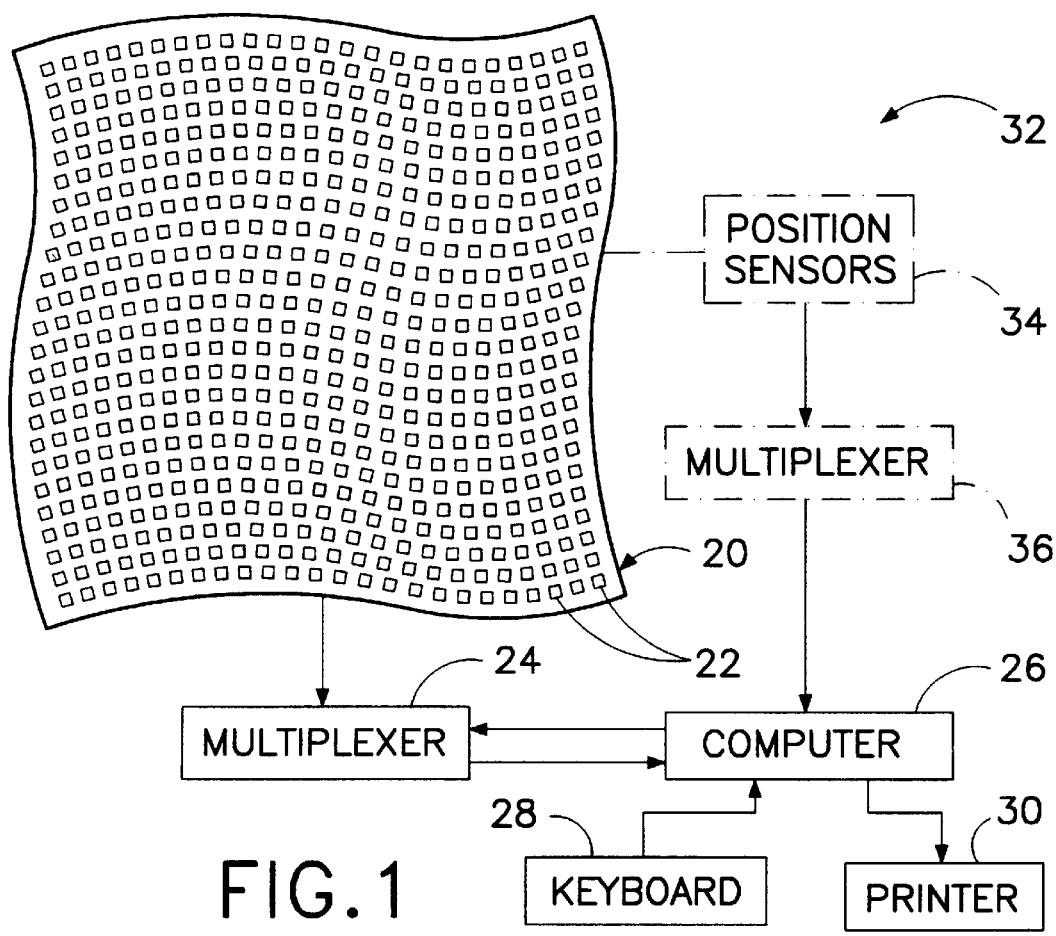
FIG. 1 is partially a schematic bottom plan view and partially a block diagram of a nuclear medicine diagnostic apparatus in accordance with the present invention, showing a sensor carrier in the form of a flexible web.

As illustrated in FIG. 1, a nuclear medicine diagnostic apparatus comprises a flexible carrier web 20 to which are attached a plurality of rigid substrates 22 each bearing at least one solid-state gamma ray sensor (not separately shown, not separately designated). Gamma ray sensors 22 are operatively connected via a switching circuit or multiplexer 24 to a computer 26 for transmitting thereto signals used by the computer in deriving information about location and size of a source of radioactivity in a patient about which the carrier web 20 is wrapped in a generally cylindrical configuration. The flexibility of carrier web 20 enables disposition of different gamma ray sensors 22 on different sides of the patient so that the sensors at least partially surround the patient. The generally cylindrical use configuration of carrier web 20 has a diameter which depends on the size of the particular portion of a patient which is being investigated via radioactive tagging.

In use of the nuclear medicine diagnostic apparatus of FIG. 1, a patient is supplied with an injected or ingested radioactive composition which is keyed for take-up or absorption by a particular target organ or tissue body of the patient. After an interval allowing selective absorption of the radioactively tagged composition by the target organ or tissue body, carrier web 20 is wrapped at least partially about the portion of the patient containing the target organ or tissue body. That portion of the patient's body may be, for example, the chest, abdomen, or neck of the patient.

In many cases, the information required for diagnosis is merely the degree to which the radioactive composition is absorbed by the target organ or tissue body. In that case, computer 26 processes the signals from sensors 22 to measure the intensity of radiation emanating from the patient. Because sensors 22 effectively surround the patient, the nuclear medicine apparatus of FIG. 1 provides an accurate proportional measurement of the amount of radioactive composition absorbed by the target organ or tissue body in the patient. Where the location of the target organ or tissue body is known, the proportional measurement may be refined to an exact magnitude. Computer 26 is provided with a customary input device such as a keyboard 28 and a conventional output device such as a printer 30 for respectively receiving instructions from and providing results to an operator. The nuclear medicine apparatus of FIG. 1 optionally includes an auxiliary system 32 for determining the positions of gamma ray sensors 22 relative to one another upon application of carrier web 20 to a patient. This positioning system includes position sensors 34 operatively connected to carrier web 20 for generating, in real time, signals containing position data. These signals are transmitted to computer 26 via a switching circuit or multiplexer 36.

Figure 2:
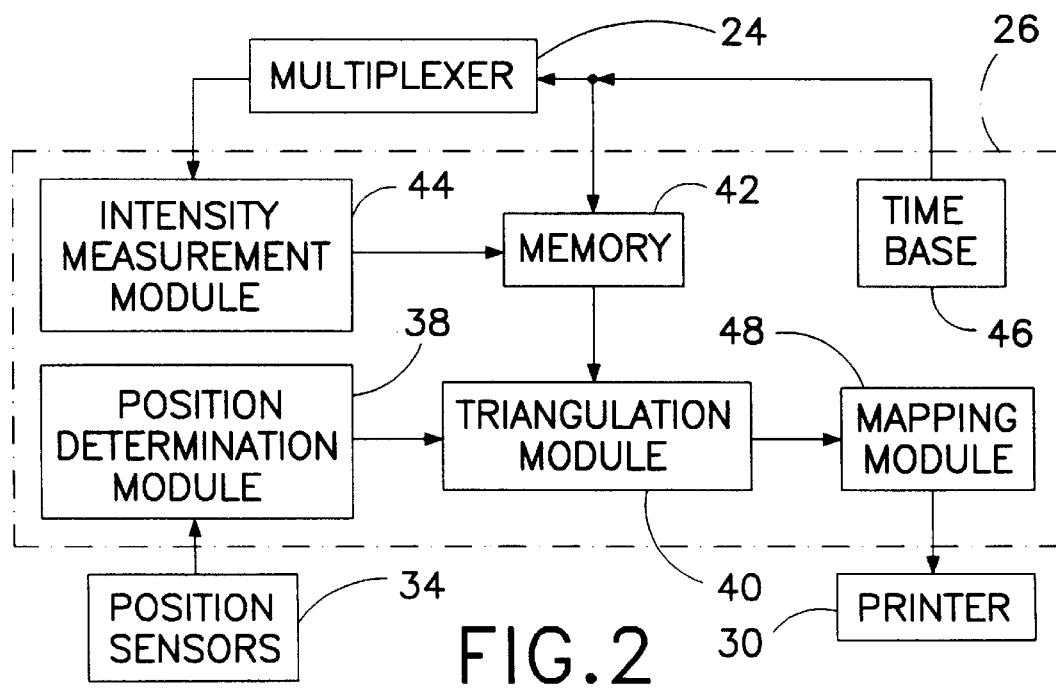
FIG. 2 is a block diagram depicting functional modules of a computer included in the apparatus of FIG. 1.

As illustrated in FIG. 2, computer 26 includes a position determination module 38 which receives the data signals from position sensors 34 and calculates the positions of sensors 22. The calculated sensor positions are transmitted from position determination module 38 to a triangulation module 40. Triangulation module 40 receives from a memory 42 of computer 26 radiation intensity data stored in the memory by an intensity measurement module 44 under the control of a time base 46. Module 44 is connected to the various sensors 22 of web 20 via multiplexer 24 and essentially converts the signals from the sensors into instantaneous intensity measurements stored in memory 42 in locations corresponding to the respective sensors, as determined by time base 46.

Triangulation module 40 executes a series of triangulation calculations based on well-known variation of intensity with distance to determine the location of each incremental volume of organic tissues which emits radiation of a frequency or frequencies characteristic of the particular radioactive compound supplied to the patient. From the collection of incremental volumes, a mapping module 48 connected to triangulation module 40 constructs the three-dimensional shape, size and location of one or more regions of internal organic tissues emitting the characteristic radiation. The resolution or accuracy of the contours of each detected target region is determined largely by the number and size of the solid-state radiation sensors 22. The higher the density of sensors 22, i.e., the smaller the sensors, the finer the resolution of the shape determination. Generally sensors 22 will have an identical size (and shape), although different sizes could be accommodated by signal processing.

Mapping module 48 is connected to printer 30, and/or to some other output peripheral unit such as a monitor (not shown), for purposes of communicating to a user the shape, size and location of a detected radioactive target region in a patient. An image may be presented to the user showing the detected target region by itself or in relation to internal organs and tissue structures of the patient, for example, as described hereinafter with reference to an ancillary ultrasonic imaging system.

Figures 3, 4:
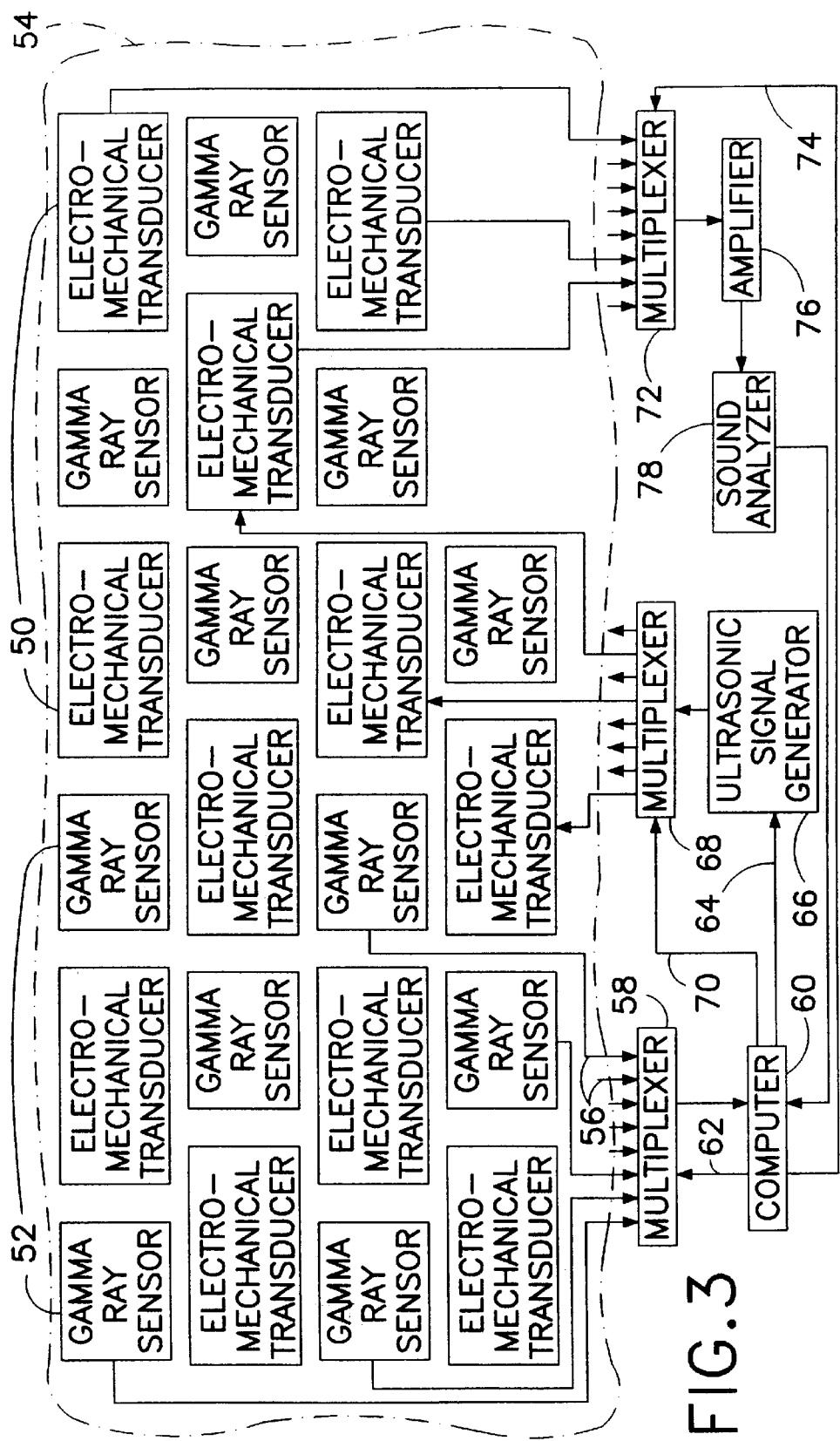
FIG. 3 is a block diagram of another nuclear medicine diagnostic apparatus in accordance with the present invention, incorporating an ultrasonic imaging system with position sensors in the form of electromechanical transducers.
FIG. 4 is a schematic cross-sectional view showing an alternative specific configuration of a sensor carrier in accordance with the present invention.

FIG. 3 is a block diagram of a nuclear medicine diagnostic apparatus incorporating an ultrasonic imaging system with position sensors in the form of electromechanical transducers 50. Transducers 50, as well as a multiplicity of solid-state gamma ray sensors 52, are connected to a flexible web 54. Gamma ray sensors 52 have output leads 56 extending to a multiplexer or switching circuit 58. Multiplexer 58 is connected to a computer 60 for feeding thereto, in a sequence determined by the computer via a control lead 62, a series of signals encoding essentially instantaneous radiation intensities detected by the respective sensors 52. These intensity signals are processed by computer 60 as described above with reference to FIG. 2.

Computer 60 has an output line 64 extending to an ultrasonic signal generator 66 for controlling that unit to produce a waveform of one or more ultrasonic frequencies. The waveform is output to a switching circuit or multiplexer 68 which distributes the waveform to certain transducers 50 in accordance with a control signal supplied to multiplexer 68 via a lead 70.

Web 54 is placed in effective contact with the patient so that ultrasonic pressure waves generated by excited transducers 50 in response to the waveform from generator 66 are transmitted into the patient. These ultrasonic pressure waves are differentially reflected by internal tissue structures of the patient, the reflected waves being sensed by a receiving subset of transducers 50. The sensed pressure waves are converted into electrical signals by the receiving transducers 50. The electrical signals are sampled or interrogated by a switching circuit or multiplexer 72 in response to a control signal transmitted from computer 60 over a lead 74. Multiplexer 72 passes the sampled signals to a digitizing amplifier 76 in turn connected at an output to a sound analyzer 78. Analyzer 78 preprocesses the ultrasonic waves to facilitate a construction of three-dimensional shapes or models of internal tissue structures of the patient by computer 60.

As illustrated schematically in FIG. 3, transducers 50 and sensors 52 may be disposed adjacent to one another in a single layer of web 54. Alternatively, as depicted in FIG. 4, transducers 50 and sensors 52 may be disposed in different layers 80 and 82 of web 54.

Figure 5:
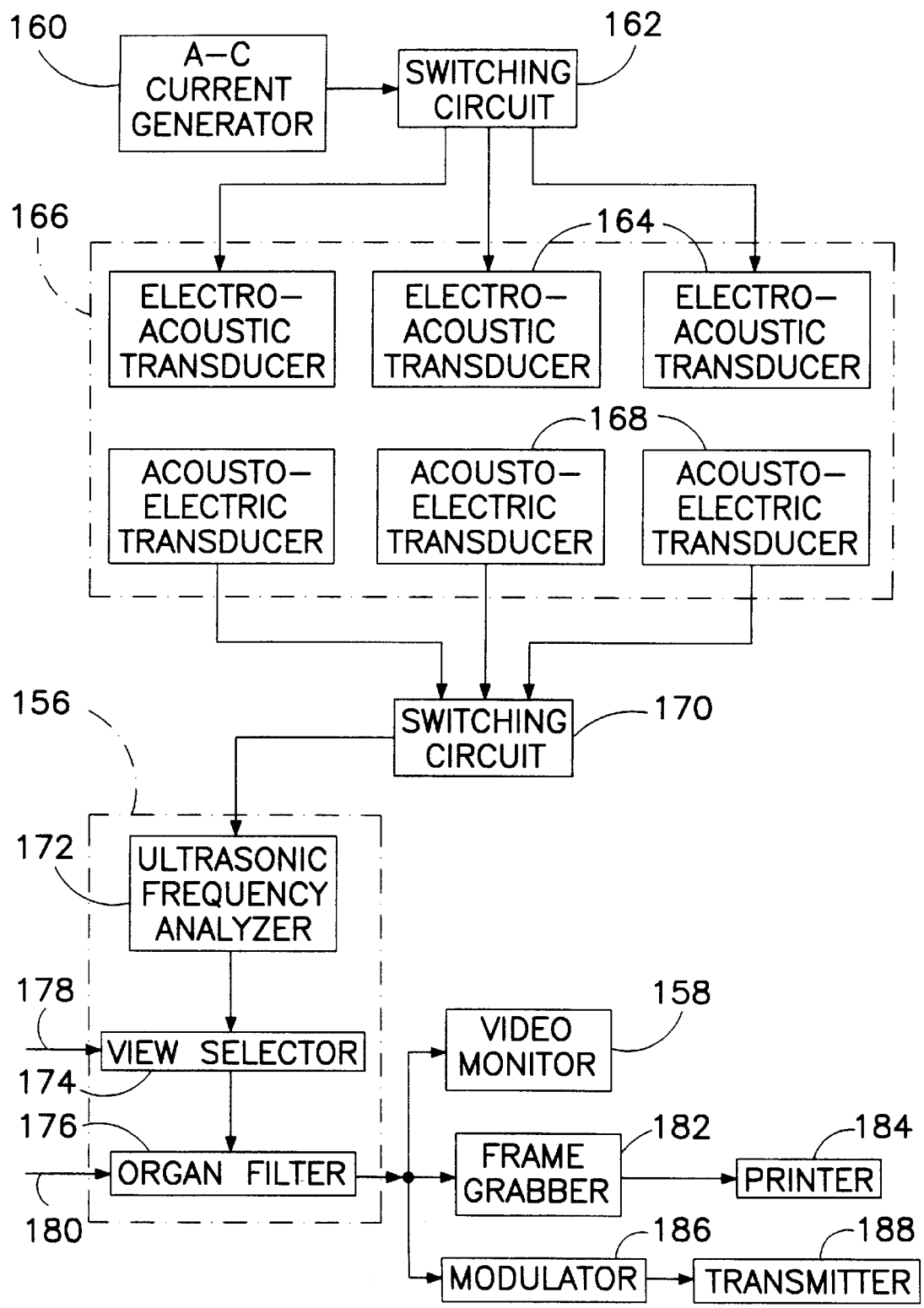
FIG. 5 is a block diagram of an ultrasonic imaging system similar to that shown in FIG. 3, for use in diagnostic and therapeutic procedures in conjunction with a nuclear medicine diagnostic apparatus in accordance with the present invention.

FIG. 5 illustrates a modification of the nuclear medicine diagnostic apparatus of FIG. 3, particularly with respect to the ultrasonic imaging system thereof. A control unit 156, which incorporates the triangulation module 40 and mapping module 48 of FIG. 2, sequences the switching operations of multiplexers 58 and 72 and constructs three-dimensional electronic models of internal organs and tissue structures of a patient from preprocessed ultrasonic data is connected at an output to a video monitor 158. Control unit 156 transmits to video monitor 158 a video signal which, when used to display an image on the monitor, depicts selected internal organs and tissue structures from a selected angle or viewpoint. The image may incorporate a representation of the radioactive target region identified by the computer as discussed above with references to FIGS. 1 and 2.

As further illustrated in FIG. 5, an a–c current or ultrasonic signal generator 160 is connected via a multiplexer or switching circuit 162 to different piezoelectric type electroacoustic transducers 164 in seriatim. Transducers 164 are mounted in interspaced fashion to a flexible web 166 which also carries an array of spaced piezoelectric type acoustoelectric transducers 168.

Web 166 is placed adjacent to a skin surface of a patient. In some cases, with any of the ultrasonic sensing devices described herein as ancillary to a nuclear medicine diagnostic apparatus, it may be beneficial to provide a layer of fluid (e.g., water, gel) between the skin surface of the patient and the respective transducer carrier (e.g., web 166) to facilitate ultrasonic wave transmission from the electroacoustic transducers to the patient and from the patient back to the acoustoelectric transducers or sensors. In some specific embodiments of an ultrasonic imaging device discussed herein, a fluid-filled bag is used to optimize pressure wave transmission between a transducer carrier and a skin surface of a patient. Another kind of interface facilitating ultrasonic wave conduction is a moldable solid or semisolid such as wave-conductive plastic material, known in the art.

In response to the periodic energization of transducers 164, ultrasonic pressure waves are reflected from internal organic structures of the patient and sensed by acoustoelectric transducers 168. Electrical signals generated by transducers 168 in response to the reflected pressure waves are fed via a multiplexer or switching circuit 170 to control unit 156.

Control unit 156 controls switching circuits 162 and 170 to energize emitting transducers 164 in a predetermined sequence and to selectively couple receiving transducers 168 in a pre-established sequence to a pressure wave or ultrasonic frequency analyzer 172 in control unit 156. The sequencing depends in part on the portion of the patient being monitored. In some cases, this sequencing of transducer excitation and of sensor sampling or interrogation may effectuate a phased array volumetric scan of internal bodies tissues.

More specifically, the sequence in which receiving transducers 168 are sampled or interrogated by switching circuit

170 may organize sensor response into predetermined groupings defining respective data gathering apertures. The grouping of sensors or transducers 168 may be an instantaneous grouping, varied instant by instant pursuant to real-time imaging requirements. Generally, the larger the apertures (the larger the areas of the respective sensor groupings), the higher the resolution of the three-dimensional ("3D") volumetric data acquisition and of the imaging of the system. Control unit 156 and particularly ultrasonic frequency analyzer 172 thereof operates to coherently combine structural data from the respective apertures, with the execution of a self-cohering algorithm which computes the relative positions and orientations of receiving transducers 168 using instantaneous position measurements and which adjusts the signals from the coherently combined apertures so they can be added together constructively. The resultant effective increase in total aperture size improves the resolution capability of the imaging system. Control unit 156 may also include the option of noncoherently combining structural data, which allows extended images to be created without increasing the imaging resolution. The sequencing of transducer energization or excitation, as well as the sampling of outputs of sensors, may also be carried out to execute a phased-array-type electronic scan of internal tissues.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view.

Filter stage 176 is operatively connected to analyzer 172 and video monitor 158 for optionally eliminating a selected organ from the displayed image. Filter stage 176 is provided with an input 180 from a keyboard (28, FIG. 1) or other operator interface device for enabling an operator to select an organ for deletion from the displayed image. In one example of the use of filter stage 176, blood moving through a vessel of the vascular system is deleted to enable viewing of the blood vessel walls on monitor 158. This deletion is easily effected starting from conventional techniques such as the Doppler detection of moving bodies.

Filter stage 176 may also function to highlight selected organs or tissue structure, for instance, a radioactive region detected by computer 156 in response to signals from gamma ray sensors 50 (FIG. 3). Pattern recognition techniques may be used by computer 156 to identify organic structures located about the detected radioactive region. In executing a pattern recognition routine, computer 156 compares, with prestored electronically encoded forms, three-dimensional shapes detected by ultrasonic scanning. Highlighting of selected organic structures may be implemented exemplarily through color, intensity, cross-hatching, or outlines.

As further illustrated in FIG. 5, control unit 156 is optionally connected at an output to a frame grabber 182 for selecting a particular image for reproduction in a fixed hard copy via a printer 184. In addition, nuclear medicine diagnostic results and ultrasonically derived real-time image information may be encoded by a modulator 186 onto a carrier wave sent to a remote location via a wireless transmitter 188.

FIG. 6 depicts the apparatus of FIG. 5 in a form wherein control unit 156 (FIG. 5) is realized as a specially programmed general purpose digital computer 190. A switching circuit or multiplexer 192 relays signals incoming from respective acoustoelectric transducers 168 (FIG. 5) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 5). A filter module 204 is provided for removing selected organs from the image presented on the visual display or video monitor 158. Sampling circuit 198, wave analysis module 200, view selection module 202, and filter module 204 are program-modified generic digital circuits of computer 190.

FIGS. 7 and 8 depict a specialized sensor web 232 in the form of a garment such as a vest. Sensor vest 232 carries solid-state gamma ray sensors (not illustrated in FIG. 7 or 8) as discussed above. The gamma ray sensors or radioactivity detectors may be distributed throughout the vest in an alternating sequence with electromechanical ultrasonic pressure wave transducers, as shown in FIG. 3. Alternatively, vest 232 may have different layers, one for the ultrasonic pressure wave transducers and another for the gama ray sensors or radioactivity detectors. Computer 246 incorporates functional modules as disclosed herein with reference to FIG. 2, for determining the size, shape and location of a radioactive region in a patient. Those functional modules are realizable by generic digital computer circuits modified by programming.

Sensor vest 232 has arm holes 234 and 236, a neck opening 238 and fasteners 240 for closing the vest about a patient. In addition, sensor vest 232 is provided with a plurality of elongate chambers 242 which receive fluid for expanding the vest into conformation with a patient's skin surface, thereby ensuring contact of the vest with a patient's skin surface and facilitating the transmission of ultrasonic pressure waves to and from ultrasonic transducers 244. FIG. 7 shows a computer 246, a video monitor 248 and a printer 250 used as described above.

Sensor vest 232 may be understood as a container assembly having fluid-filled chambers 242 with flexible inwardly facing walls (not separately designated) which conform to the patient. Sensor vest 232 may additionally be provided along an inner side with a conventional interface medium, whether water, gel, plastic or some other material, which is conducive to the transmission of ultrasonic vibrations across the interface between the patient and the sensor vest.

Figure 9:
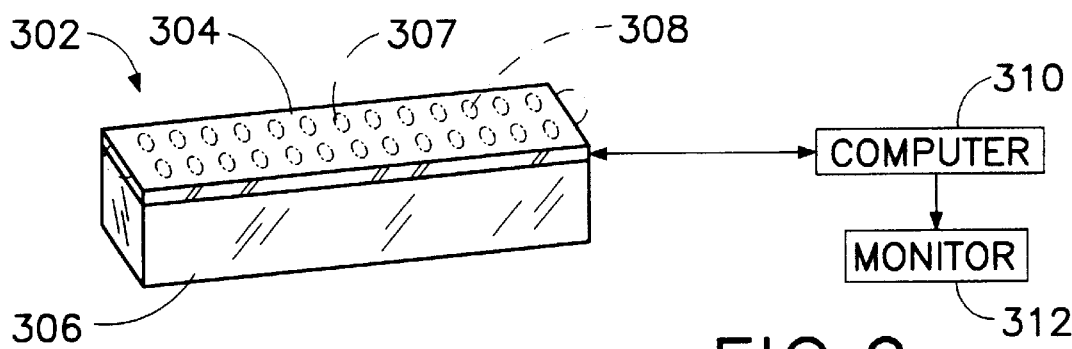
FIG. 9 is partially a schematic perspective view and partially a block diagram of another nuclear medicine diagnostic apparatus incorporating an ultrasonic diagnostic imaging system.
Figure 10:
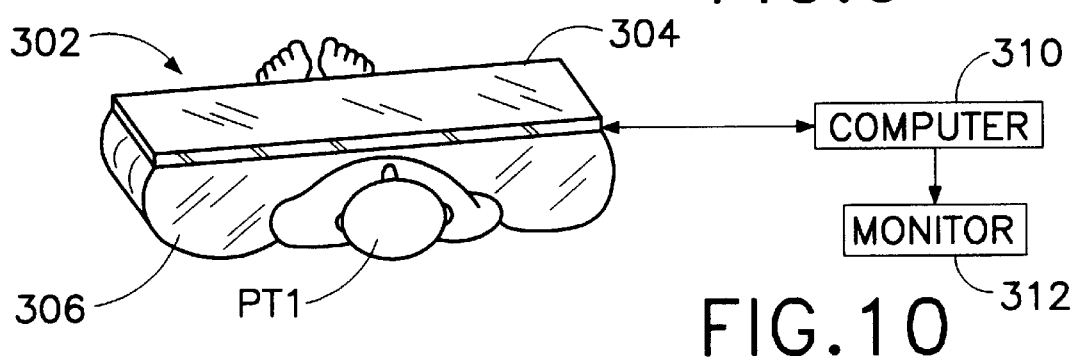
FIG. 10 is partially a schematic perspective view and partially a block diagram of diagnostic apparatus of FIG. 9, showing the apparatus in use with a patient.

As illustrated in FIG. 9, a nuclear medicine diagnostic apparatus comprises a container assembly 302 including a substantially rigid plate 304 attached to a flexible bladder or bag 306. Bladder or bag 306 is filled with a liquid and is sufficiently flexible to substantially conform to a patient when the container assembly 302 is placed onto a patient PT1, as illustrated in FIG. 17. A liquid or gel or other interface medium may be deposited on the patient prior to the placement of container assembly 302 on patient PT1.

Plate 304 is provided with multiple gamma ray sensors or radioactivity detectors 307 and multiple ultrasonic pressure wave generators and detectors 308 and 309 as described above with respect to FIGS. 7 and 8. Sensors 307, generators 308, and detectors 309 are connected to a computer 310 having essentially the same functional structures and programming as computer 190 for (a) implementing sequential generator energization and sequential detector sampling, (b) determining sensor positions, (c) constructing three-dimensional electronic models of internal organic structures, and (d) mapping the shape, size and location(s) of one or more internal radioactive regions, as described above. Computer 310 is connected to a monitor 312 for displaying images of internal organs of patient PT1, including images or detected radioactive regions. Computer 310 has the capability of alternately displaying organ images from different angles, as discussed above. In particular, the radioactive regions may be viewed from different angles.

Ultrasonic pressure wave generators 308 and detectors 309 may be densely packed and energized or interrogated as individual elements separately from each other. Coherent aperture combining is not used in such an operating mode. Alternatively, the ultrasonic pressure wave detectors 308 may be sampled or interrogated in groups, permitting the formation of a plurality of data gathering apertures. In that case, computer 310 may coherently combine structural data from the different apertures to thereby increase focusing power or resolution.

Plate 304 may be formed as a rectangular array of rigid modular substrates rigidly connected to one another, each of the substrates incorporating respective sensors 307, generators 308, and detectors 309.

Figure 11:
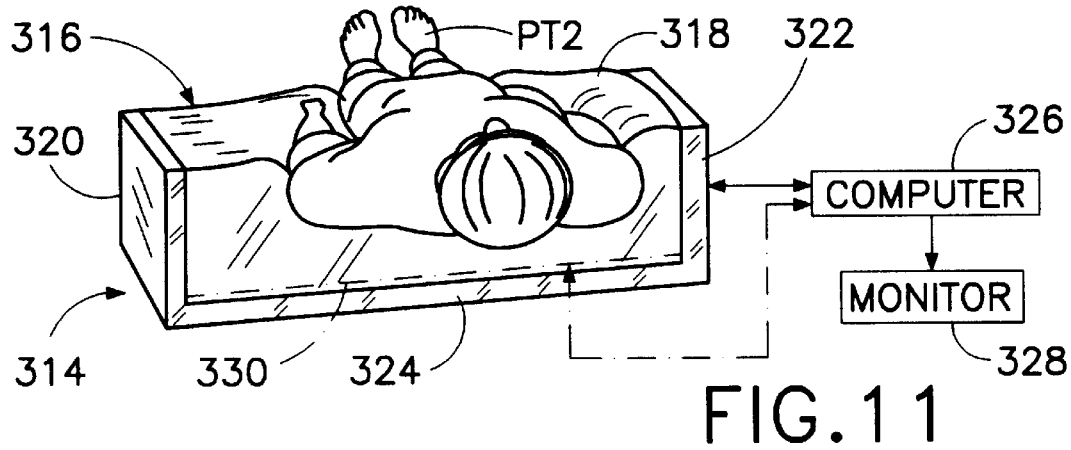
FIG. 11 is partially a schematic perspective view and partially a block diagram of another nuclear medicine diagnostic apparatus incorporating an ultrasonic imaging device, in accordance with the present invention, showing the apparatus in use with a patient.

FIG. 11 depicts another nuclear medicine diagnostic apparatus with ultrasonic determination of sensor positions and three-dimensional internal organic structures. The apparatus comprises a container assembly 314 which includes a fluid-filled sack or bag 316 for receiving a patient PT2. Sack or bag 316 includes a flexible upper wall 318 which deforms to conform to the patient PT2 upon placement of the patient onto the bag. Bag 316 is supported on two or more sides by substantially rigid walls or panels 320 and 322. Panels 320 and 322 are either integral with bag 316 or separable therefrom. Panels 320 and 322, as well as an interconnecting bottom panel 324, may be provided with multiple solid-state gamma ray sensors (not shown) and ultrasonic pressure wave generators and detectors (not shown) as described above with respect to FIGS. 7 and 8, and FIG. 9. These sensors, generators, and detectors are connected to a computer 326 having essentially the same functional structures and programming as computer 190 for (a) implementing sequential generator energization and sequential detector sampling, (b) determining sensor positions, (c) constructing three-dimensional electronic models of internal organic structures, and (d) mapping the shape, size and location(s) of one or more internal radioactive regions, as described above. Computer 326 is connected to a monitor 328 for displaying images of internal organs of patient PT2, including images or detected radioactive regions. Computer 326 has the capability of alternately displaying organ images from different angles, as discussed above. In particular, the radioactive regions may be viewed from different angles.

The gamma ray sensors and the ultrasonic pressure wave generators and detectors may be disposed in a wall panel of bag 316 or may be provided in a separate carrier 330 disposable, for example, between bottom panel 324 and bag 316, as shown in FIG. 11.

The ultrasonic pressure wave generators and detectors may be densely packed and energized or interrogated as individual elements separately from each other. Coherent aperture combining is not used in such an operating mode. Alternatively, the ultrasonic pressure wave detectors may be sampled or interrogated in groups, permitting the formation of a plurality of data gathering apertures. In that case, computer 326 may coherently combine structural data from the different apertures to thereby increase focusing power or resolution.

Figure 12:
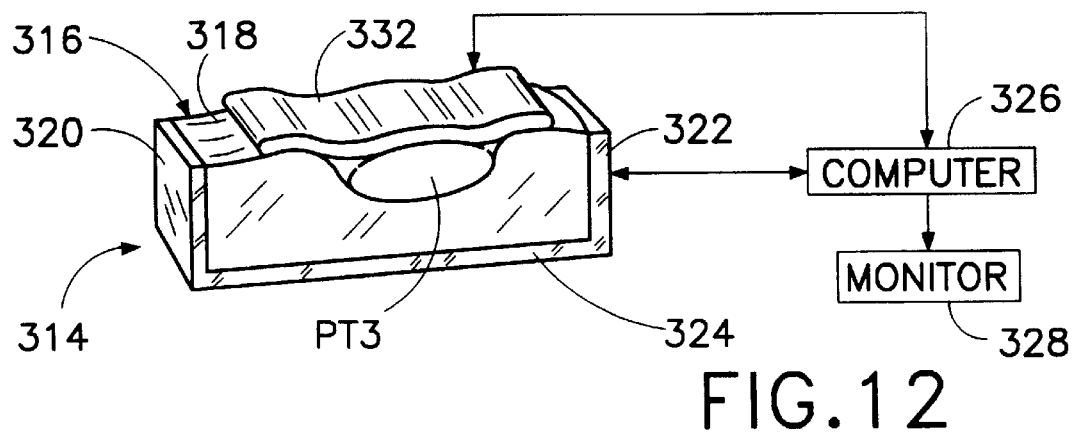
FIG. 12 is partially a schematic perspective view and partially a block diagram of the nuclear medicine apparatus of FIG. 11, showing a modification of the nuclear medicine diagnostic apparatus of FIG. 11.

As illustrated in FIG. 12, the nuclear medicine diagnostic apparatus of FIG. 11 may be used in conjunction with a flexible web or cover sheet 332 carrying electromechanical pressure wave transducers and solid-state gamma ray detectors. Web or cover sheet 332 is operatively connected to computer 326 for providing ultrasonically derived organ position and configuration data to the computer for displaying organ images on monitor 328. The use of web or sheet 332 enables the disposition of gamma ray sensors and ultrasonic wave generators and detectors in a 360° arc about a patient PT3 (diagrammatically illustrated in FIG. 12), thereby facilitating image production.

As discussed above, to contact surfaces a liquid, gel or other conductive medium is applied to facilitate ultrasonic pressure wave transmission over interfaces.

As discussed hereinafter with reference to FIG. 13, video monitor 158 (FIG. 5) or monitor 328 (FIG. 12) may take the form of a flexible video screen layer attached to web 20, 54, 166 or 206 (FIGS. 1, 3, 5) or web 332 (FIG. 12). This modification of the imaging component of the nuclear medicine diagnostic devices discussed above is considered to be particularly advantageous in medical diagnosis procedures. The web or substrate with the video screen is disposed on a selected body portion of a patient, for example, the abdomen or neck, so that the substrate and the video screen layer substantially conform to the selected body portion and so that the video screen is facing away from the body portion.

Figure 13:
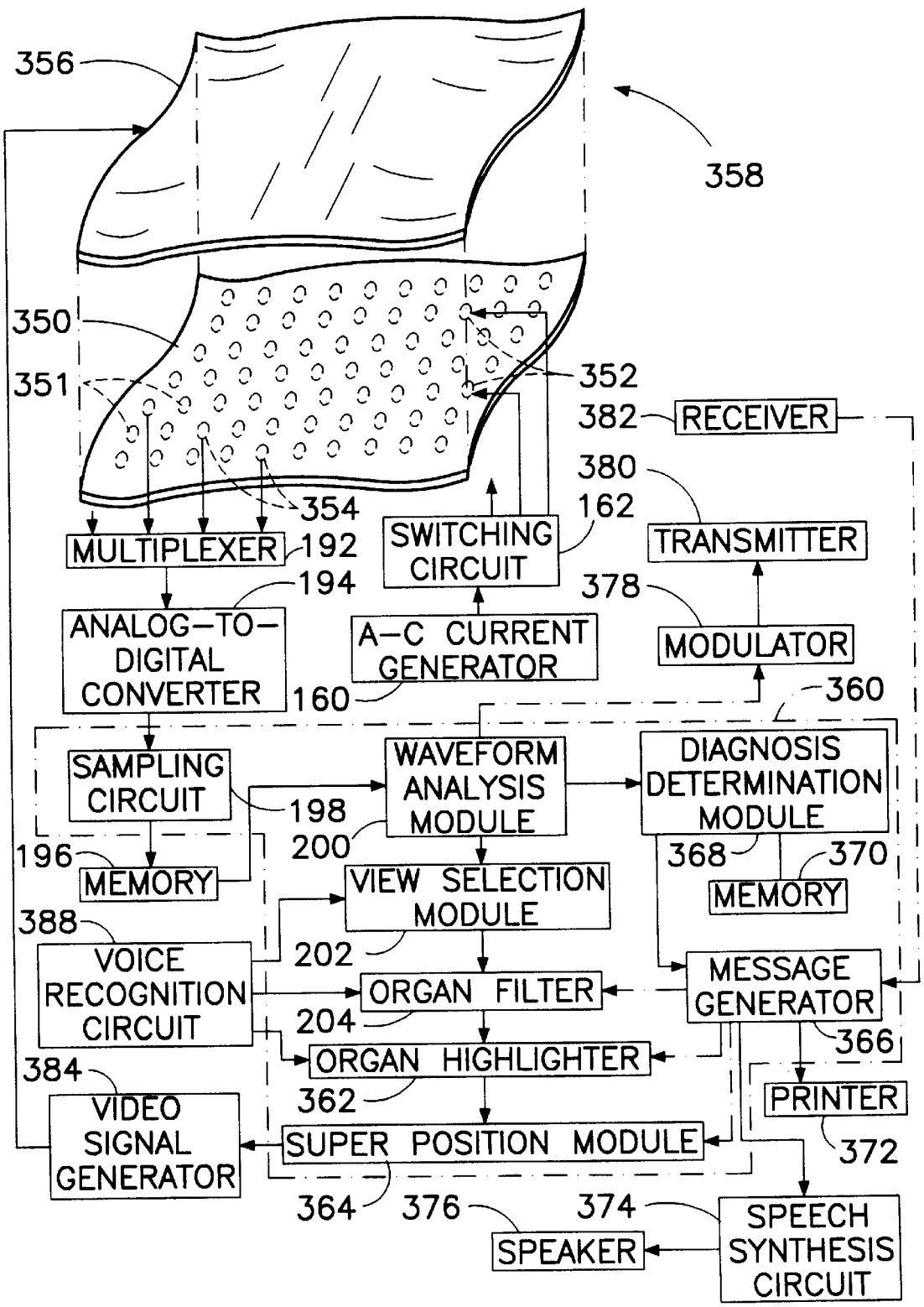
FIG. 13 is partially a schematic exploded perspective view and partially a block diagram of an ultrasonographic system utilizable in conjunction with a nuclear medicine apparatus in accordance with the present invention.

As shown in FIG. 13, a nuclear medicine diagnostic apparatus or system comprises a flexible substrate or web 350 which carries a plurality of solid-state nuclear medicine sensors 351, a plurality of piezoelectric electroacoustic transducers 352, and a plurality of piezoelectric acousto-electric transducers 354. A flexible video screen 356 is attached to substrate or web 350 substantially coextensively therewith. Video screen 356 may be implemented by a plurality of laser diodes (not shown) mounted in a planar array to a flexible carrier layer (not separately designated). The diodes are protected by a cover sheet (not separately illustrated) which is connected to the carrier layer. Energization componentry is operatively connected to the diodes for energizing the diodes in accordance with an incoming video signal to reproduce an image embodied in the video signal. In a video monitor, the laser diodes are tuned to different frequency ranges, so as to reproduce the image in color. The protective cover sheet may function also to disperse light emitted by the laser diodes, to generate a more continuous image.

Substrate or web 350 and video screen 356 comprise an nuclear medicine video coverlet 358 which may be used with the control hardware depicted in FIGS. 1, 2, 5 and 6. Reference numerals used in FIGS. 5 and 6 are repeated in FIG. 13 to designate the same functional components.

Electroacoustic transducers 352 are connected to a–c or ultrasonic signal generator 160 for receiving respective a–c signals of variable frequencies. Generator 160 produces frequencies which are directed to the electroacoustic transducers 352 by switching circuit 162. Pressure waveforms of different ultrasonic frequencies have different penetration depths and resolutions and provide enhanced amounts of information to a digital signal processor or computer 360. As discussed above with reference to computer 190 of FIG. 6, computer 360 is a specially programmed digital computer wherein functional modules are realized as generic digital processor circuits operating pursuant to preprogrammed instructions.

As discussed above with reference to FIG. 6, switching circuit or multiplexer 192 relays signals incoming from respective acoustoelectric transducers 354 in a predetermined intercalated sequence to analog-to-digital converter 194, the output of which is stored in computer memory 196 by sampling circuit 198. Acoustoelectric transducers 354 may be interrogated by multiplexer 192 and sampling circuit 198 in such a sequence as to enable or facilitate a grouping of transducers 354 to form a plurality of data gathering apertures. Waveform analysis module 200 retrieves the digital data from memory 196 and processes the data to perform a 3D volumetric data acquisition of the internal tissue structures, thereby determining three dimensional organic structures inside a patient. Waveform analysis module 200 includes coherent aperture combining circuitry for coherently combining structural data from the respective apertures. Wave analysis module 200 also includes position determination circuitry which executes computations according to a self-cohering algorithm that computes the relative positions and orientations of transducers 354 using instantaneous position measurements and adjusts the signals from the coherently combined apertures so they can be added together constructively. Owing to a more or less dense packing of sensors 351, electroacoustic transducers 352, and acoustoelectric transducers 354, the position measurements of wave analysis module 200 serve also to determine the locations of sensors 351 (the function of position determination module 38 of FIG. 2). Analysis module 200 may also include the option of noncoherently combining structural data, which allows extended images to be created without increasing the imaging resolution.

The three-dimensional structural data generated by waveform analysis module 200 in response to ultrasonic feedback from internal organs of a patient is provided to view selection module 202 for deriving two-dimensional images for display on video screen 256. Filter module 204 serves to remove selected organs, for example, overlying organs, from the image presented on video screen 356. Sampling circuit 198, wave analysis module 200, view selection module 202, and filter module 204 are program-modified generic digital circuits of computer 360.

Computer 360 contains additional functional modules, for example, an organ highlighter 362 and a superposition module 364. The functions of organ highlighter 362 are discussed above with reference to organ filter 176 and 204 in FIGS. 5 and 6. Mapping module 48 (FIG. 2) may be connected to view selection module 202, organ filter 204 and organ highlighter 362 so that the functions of those modules may operate on the structural information as to detected radioactive regions in the patient.

Organ highlighter 362 operates to provide a different color or intensity or cross-hatching to different parts of an image to highlight a selected image feature. For example, a detected radioactive region may be shown with greater contrast than surrounding organs, thereby facilitating perception of the highlighted region on video screen 356. After organ filter 204 has removed one or more selected organs from an electronic signal representing or encoding an image of internal organs, highlighter 362 operates to highlight one or more features of the encoded image.

Superposition module 364 effects the insertion of words or other symbols on the image displayed on video screen 356. Such words or symbols may, for example, be a diagnosis or remark pertaining to the location, shape and size of a detected radioactive region. Alternatively and supplementarily, such words or symbols may, for example, be a diagnosis or alert signal produced by a message generator module 366 of computer 360 in response to a diagnosis automatically performed by a determination module 368 of computer 360. Module 368 receives the processed image information from waveform analysis module 200 and consults an internal memory 370 in a comparison or pattern recognition procedure to determine whether any organ or internal tissue structure of a patient has an abnormal configuration. The detection of such an abnormal configuration may be communicated to the physician by selectively removing organs, by highlighting organs or tissues, or superimposing an alphanumeric message on the displayed image. Accordingly, message generator 366 may be connected to organ filter 204 and organ highlighter 362, as well as to superposition module 364. The communication of an abnormal condition may be alternatively or additionally effectuated by printing a message via a printer 372 or producing an audible message via a speech synthesis circuit 374 and a speaker 376.

As discussed above, the nuclear medicine diagnostic results may be transmitted over a telecommunications link (not shown in FIG. 13) via a modulator 378 and a transmitter 380. The transmitted information may be processed at a remote location, either by a physician or a computer, to generate a further diagnosis or treatment recommendation. This diagnosis or recommendation may be encoded in an electrical signal and transmitted from the remote location to a receiver 382. Receiver 382 is coupled with message generator module 366, which can communicate the diagnosis or other message as discussed above.

Computer 360 is connected at an output to a video signal generator 384 (which may be incorporated into the computer). Video signal generator 384 inserts horizontal and vertical synchronization signals and transmits the video signal to video screen 356 for displaying an image of internal patient organs thereon.

Although the invention has been described in terms of particular embodiments and applications, one of ordinary skill in the art, in light of this teaching, can generate additional embodiments and modifications without departing from the spirit of or exceeding the scope of the claimed invention. For example, it is to be noted that other kinds of systems, other than the ultrasonic transducer arrays and associated processing circuitry disclosed herein, may be used to determine the relative positions of multiple solid-state radioactivity detectors. The simplest kind of position determination system is a rigid carrier. In that case, the positions of all of the solidstate radioactivity detectors or gamma ray sensors relative to the coordinate system of the rigid carrier are known. A rigid carrier, in accordance with the present invention may be partially or substantially cylindrical, in order to conform to the body part which is to be scanned for radioactive emissions. A standard one-size-fits-all cylindrical array of solid-state radioactivity detectors or gamma ray sensors is large enough to accommodate essentially the largest possible patient torso. Of course, multiple detector or sensor carriers may be provided for body parts of different kinds and sizes.

In the case of a flexible or internally movable carrier body, the position sensing system may be optical. For example, multiple interferometric metrology devices, or directional optical fringe counters, may be attached to substrates of the gamma ray sensors for measuring changes in relative positions of adjacent sensors. Alternatively, the carrier body may be illuminated with an optical grid which is distorted due to the irregular surfaces of the carrier body and the patient. An image captured by one or more cameras is analyzed by computer to determine the shape causing the apparent distortions in the shape of the optically generated grid.

Accordingly, it is to be understood that the drawings and descriptions herein are proffered by way of example to facilitate comprehension of the invention and should not be construed to limit the scope thereof.

What is claimed is:

1. A medical diagnostic apparatus comprising:
    a carrier body disposable in any of a plurality of nonplanar configurations so as to at least partially surround a portion of a patient;
    a plurality of rigid substrates each bearing at least one solid-state gamma ray sensor, said substrates being movably attached to each other via said carrier body;
    a computer operatively connected to said sensors for receiving signals therefrom and deriving information about location and size of a source of radioactivity in the patient; and
    means for actively determining the positions of the gamma ray sensors relative to one another and relative to the patient upon a disposition of said carrier body relative to the patient.

2. The apparatus defined in claim 1 wherein said carrier body is flexible and substantially conformable to the patient.

3. The apparatus defined in claim 1 wherein said means for actively determining includes position sensors operatively connected to said computer.

4. The apparatus defined in claim 3 wherein said means for actively determining further includes a position determination module in said computer operatively linked to said position sensors for calculating the positions of said gamma ray sensors from data provided by said position sensors.

5. A medical diagnostic device comprising:
    a plurality of solid-state radioactivity sensors;
    carrier means attached to said sensors for enabling disposition of said sensors in any of a plurality of different nonplanar configurations relative to a patient;
    position sensors for determining the positions of said radioactivity sensors relative to one another upon a placing of said carrier means in any one of said configurations; and
    a position calculation unit operatively connected to said position sensors for computing positions of said radioactivity sensors relative to each other.

6. The device defined in claim 5 wherein said carrier means includes at least one movable connector element attached to said radioactivity sensors for movably coupling said radioactivity sensors to one another.

7. The device defined in claim 6 wherein said radioactivity sensors are movably attached to one another so as to allow at least a pivoting motion of each radioactivity sensor relatively to a respective one other of said radioactivity sensors.

8. The device defined in claim 7 wherein said connector element is a flexible substrate conformable to a skin surface of a patient, said radioactivity sensors being attached in a predetermined array to said flexible substrate.

9. The device defined in claim 5 wherein said radioactivity sensors have output leads operatively connected to a computer programmed to derive information about location and size of a source of radioactivity in the patient.

10. The device defined in claim 9 wherein said position calculation unit is a module of said computer.

11. The device defined in claim 5 wherein said carrier means includes a flexible web.

12. A medical diagnostic method comprising:
    administering to a patient a chemical composition containing a radioactive isotope;
    disposing about the patient a plurality of solid-state sensors sensitive to gamma rays generated by radioactive decay of said isotope;
    conducting signals from said solid-state sensors to a computer;
    providing position sensors for sensing positions of said solid-state sensors;
    conducting signals from said position sensors to said computer; and
    operating said computer to calculate relative positions of said solid-state sensors and to derive information about location and size of a source of radioactivity in the patient from the calculated relative positions of said solid-state sensors and from the signals conducted from said solid-state sensors.

13. The method defined in claim 12 wherein the disposing of said solid-state sensors includes positioning at least two of said solid-state sensors on different sides of the patient.

14. The method defined in claim 13 wherein the disposing of said solid-state sensors includes placing said solid-state sensors in essential contact with the patient.

15. The method defined in claim 14 wherein said solid-state sensors are attached to a flexible web, the disposing of said solid-state sensors includes conforming said web to the patient.

16. The method defined in claim 12 wherein the disposing of said solidstate sensors includes placing said solid-state sensors in essential contact with the patient.

17. The method defined in claim 12 wherein said solid-state sensors are attached to a flexible web, the disposing of said solid-state sensors includes conforming said web to the patient.

* * * * *